(12) United States Patent
Burzesi

(10) Patent No.: US 11,969,275 B2
(45) Date of Patent: Apr. 30, 2024

(54) HEATABLE CONTACT SURFACE FOR USE IN MEDICAL IMAGING

(71) Applicant: XCA Composites LLC, Stephentown, NY (US)

(72) Inventor: Frank Burzesi, Stephentown, NY (US)

(73) Assignee: XCA COMPOSITES LLC, Stephentown, NY (US)

( * ) Notice: Subject to any disclaimer, the term of this patent is extended or adjusted under 35 U.S.C. 154(b) by 442 days.

(21) Appl. No.: 17/280,479

(22) PCT Filed: Sep. 27, 2019

(86) PCT No.: PCT/US2019/053507
§ 371 (c)(1),
(2) Date: Mar. 26, 2021

(87) PCT Pub. No.: WO2020/069348
PCT Pub. Date: Apr. 2, 2020

(65) Prior Publication Data
US 2022/0031261 A1    Feb. 3, 2022

Related U.S. Application Data

(60) Provisional application No. 62/737,294, filed on Sep. 27, 2018, provisional application No. 62/771,475, filed on Nov. 26, 2018.

(51) Int. Cl.
*A61B 6/00* (2006.01)
*A61B 6/04* (2006.01)
(Continued)

(52) U.S. Cl.
CPC ........... *A61B 6/045* (2013.01); *A61B 6/0414* (2013.01); *A61B 6/0442* (2013.01);
(Continued)

(58) Field of Classification Search
CPC ........... A61B 6/025; A61B 6/03; A61B 6/032; A61B 6/035; A61B 6/0414; A61B 6/0421;
(Continued)

(56) References Cited

U.S. PATENT DOCUMENTS 2,859,322 A   11/1958  Glazier et al.
3,900,654 A    8/1975  Stinger
(Continued)

FOREIGN PATENT DOCUMENTS

WO    2017129663 A1    8/2017

OTHER PUBLICATIONS

International Search Report and Written Opinion for PCT/US2019/053507, dated Dec. 16, 2019.

*Primary Examiner* — Allen C. Ho
(74) *Attorney, Agent, or Firm* — Troutman Pepper Hamilton Sanders LLP (Rochester)

(57) ABSTRACT

The present application relates to a heatable system suitable for use in a patient contacting plate used in medical imaging. The system comprises a heatable laminated structure with a plurality of layers each of which is transparent to imaging radiation and allows for thermal transfer. A heater layer, located between two of the plurality of layers, comprises an electrically resistive material and is transparent to imaging radiation. The laminated structure further includes a conductive path suitable for use in coupling a voltage source to the electrically resistive material in the heatable laminated structure, whereby the laminated structure is heated when current is passing through the conductive path. Also disclosed is a compression plate system and an imaging medical device comprising the heatable system. Methods of making the heatable system and of using it in medical imaging are also disclosed.

24 Claims, 14 Drawing Sheets

(51) Int. Cl.
*A61B 6/42* (2024.01)
*A61B 6/50* (2024.01)
*B32B 5/26* (2006.01)
*B32B 9/00* (2006.01)
*B32B 9/04* (2006.01)
*B32B 27/10* (2006.01)
*B32B 27/12* (2006.01)
*B32B 27/30* (2006.01)
*B32B 27/32* (2006.01)
*B32B 27/36* (2006.01)
*B32B 29/00* (2006.01)
*B32B 29/02* (2006.01)
*H05B 3/14* (2006.01)

(52) U.S. Cl.
CPC ............ *A61B 6/4258* (2013.01); *A61B 6/502* (2013.01); *A61B 6/54* (2013.01); *B32B 5/26* (2013.01); *B32B 9/007* (2013.01); *B32B 9/045* (2013.01); *B32B 9/047* (2013.01); *B32B 27/10* (2013.01); *B32B 27/12* (2013.01); *B32B 27/306* (2013.01); *B32B 27/32* (2013.01); *B32B 27/36* (2013.01); *B32B 29/005* (2013.01); *B32B 29/02* (2013.01); *H05B 3/145* (2013.01); *B32B 2250/40* (2013.01); *B32B 2255/205* (2013.01); *B32B 2260/023* (2013.01); *B32B 2260/046* (2013.01); *B32B 2262/106* (2013.01); *B32B 2307/202* (2013.01); *B32B 2307/206* (2013.01); *B32B 2307/732* (2013.01); *B32B 2535/00* (2013.01)

(58) Field of Classification Search
CPC ..... A61B 6/0442; A61B 6/045; A61B 6/4085; A61B 6/42; A61B 6/4208; A61B 6/4233; A61B 6/4241; A61B 6/4258; A61B 6/4283; A61B 6/44; A61B 6/4429; A61B 6/4435; A61B 6/4441; A61B 6/4447; A61B 6/4452; A61B 6/502; A61B 6/54; A61B 6/542; A61B 6/545; A61B 6/0435; A61B 6/544
USPC ...... 378/37, 62, 63, 189, 196–198, 208, 209
See application file for complete search history.

(56) References Cited

U.S. PATENT DOCUMENTS

| | | | |
|---|---|---|---|
| 4,943,986 A | 7/1990 | Barbarisi | |
| 5,081,657 A * | 1/1992 | Klawitter | A61B 6/045 219/217 |
| 5,199,056 A | 3/1993 | Darrah | |
| 5,962,348 A | 10/1999 | Bootle et al. | |
| 6,077,228 A * | 6/2000 | Schonberger | A61B 5/015 374/45 |
| 6,653,607 B2 * | 11/2003 | Ellis | A61F 7/007 219/217 |
| 6,682,484 B1 | 1/2004 | Entrekin et al. | |
| 7,508,905 B2 * | 3/2009 | Bohrisch | A61B 6/502 378/37 |
| 7,729,470 B2 * | 6/2010 | Fischer | A61B 6/045 378/208 |
| 8,089,030 B2 * | 1/2012 | Harrington | A61B 6/502 219/535 |
| 10,085,704 B2 * | 10/2018 | Kim | A61B 6/4488 |
| 11,033,242 B2 * | 6/2021 | DeFreitas | A61B 6/045 |
| 2004/0206738 A1 | 10/2004 | Argersinger et al. | |
| 2005/0287891 A1 | 12/2005 | Park | |

* cited by examiner

HEATABLE CONTACT SURFACE FOR USE IN MEDICAL IMAGING

This application is a national stage application under 35 U.S.C. § 371 of PCT Application No. PCT/US2019/053507, filed Sep. 27, 2019, which claims the priority benefit of U.S. Provisional Patent Application Ser. No. 62/771,475, filed Nov. 26, 2018, and U.S. Provisional Patent Application Ser. No. 62/737,294, filed Sep. 27, 2018, which are hereby incorporated by reference in their entirety.

FIELD

The disclosure relates generally to a heatable contact surfaces for use in medical imaging.

BACKGROUND

Medical screening, using x-rays, magnetic resonance imaging (MRI) and/or the like, is a highly effective tool for detecting diseases and evaluating one or more conditions of a patient. As part of a medical screening procedure, the patient's skin may be required to directly contact one or more surfaces of the screening device to acquire image data of a sufficient quality for evaluation. Often, a contact surface feels cold to the patient, thereby providing discomfort.

For example, in mammography, carbon fiber is used in the construction of breast platforms (digital receivers) due to the structural integrity and x-ray translucency of carbon fiber composite laminates. Another common material used for the platforms is polymethylmethacrylate (PMMA). A heating pad can be placed on the breast platform to heat it up prior to performing a mammography for the patient. However, this requires more preparation for the technician and an availability and maintenance of such heating pads.

In a conventional standard mammography examination, the breast to be examined is placed on an object table which is located at breast height of the standing or sitting patient. The object table comprises the X-ray film to be exposed together with other technical components (screens, films, detectors, filters etc.). The breast is then gently squeezed horizontally using a height-adjustable, compression plate. The breast is exposed several times from different angles, sometimes using stereotactic recordings, by briefly switching on the X-ray source. After the image recording process and/or a subsequent biopsy (removal of tissue using a hollow needle) the breast may be released again.

In mammography, the compression of the breast serves on the one hand to reduce the thickness of the breast tissue to be x-rayed, so that scatter rays are reduced. Additionally, in the examination, the breast is extended from the thorax of the patient by the compression of the breast, so a surface-proximal examination of the breast is enabled.

Normally, the compression plates and patient platform exhibit a surface temperature that coincides with the ambient temperature of the environment, normally room temperature of, for example, 20 degrees Celsius. Since the breast essentially exhibits the body temperature of the patient, i.e. approximately 37 degrees Celsius, the contact of the breast with the compression plate is perceived as uncomfortably cold by the patient.

The pain in the breast that is perceived by the patient during the compression as well as the feeling of cold occurring for the patient upon contact of the patient platform or the compression plate with the breast leads to the patient having uncomfortable associations with having a mammogram.

The present application is directed to overcoming these and other deficiencies in the art.

SUMMARY

The present application relates to a heatable system suitable for use in a patient contacting plate used in medical imaging. The system comprises a heatable laminated structure with a plurality of layers each of which is transparent to imaging radiation and allows for thermal transfer. A heater layer, located between two of the plurality of layers, comprises an electrically resistive material and is transparent to imaging radiation. The laminated structure further includes a conductive path suitable for use in coupling a voltage source to the electrically resistive material in the heatable laminated structure, whereby the laminated structure is heated when current is passing through the conductive path.

A further aspect of the present application relates to a compression plate system for use in a medical imaging system. The compression plate system includes a pair of plates between which a patient or a portion of a patient to be imaged is placed and the heatable system of the present application is mounted on one or both of the pair of plates.

Another aspect of the present application relates to a medical imaging device including the compression plate system of the present application, a voltage source coupled to the conductive path, a source of radiation directed at the patient or the portion of the patient positioned between the compression plates, and an image generating unit to produce an image of the patient or the portion of the patient positioned between compression plates. The image results from radiation directed at the patient or the portion of the patient.

A further aspect of the present application relates to a method of imaging a patient or a portion of a patient. The method includes providing the medical imaging system of the present application and placing the patient or the portion of the patient to be imaged between the compression plate system. The patient or the portion of the patient to be imaged is heated by passing current through the electrically resistive material of the heatable laminate structure from the voltage source. The patient or the portion of the patient between the compression plates is imaged.

Yet another aspect of the present application relates to a method of forming a laminate through which radiation passes. The method includes providing a plurality of layers each of which is transparent to imaging radiation and allows for thermal transfer. A heater layer comprising an electrically resistive material which is also transparent to imaging radiation is also provided. The plurality of layers and the heater layer are laminated together so that the heater layer is located between two of the plurality of layers to produce a heatable laminated structure. A conductive path is coupled to the electrically resistive material so that the laminated structure is heated when current is passing through the conductive path.

When used in medical imaging, the laminated structure of the present application can be heated to a predetermined temperature prior to contacting a patient and/or heated during such contact. Since the laminated structure can be transparent to radiation used in the medical imaging system at least in a region in which image data for evaluating the patient is acquired, the patient's experience with the imaging procedure is improved without adversely affecting the quality of the image data acquired for the patient.

DETAILED DESCRIPTION

Figure 1:
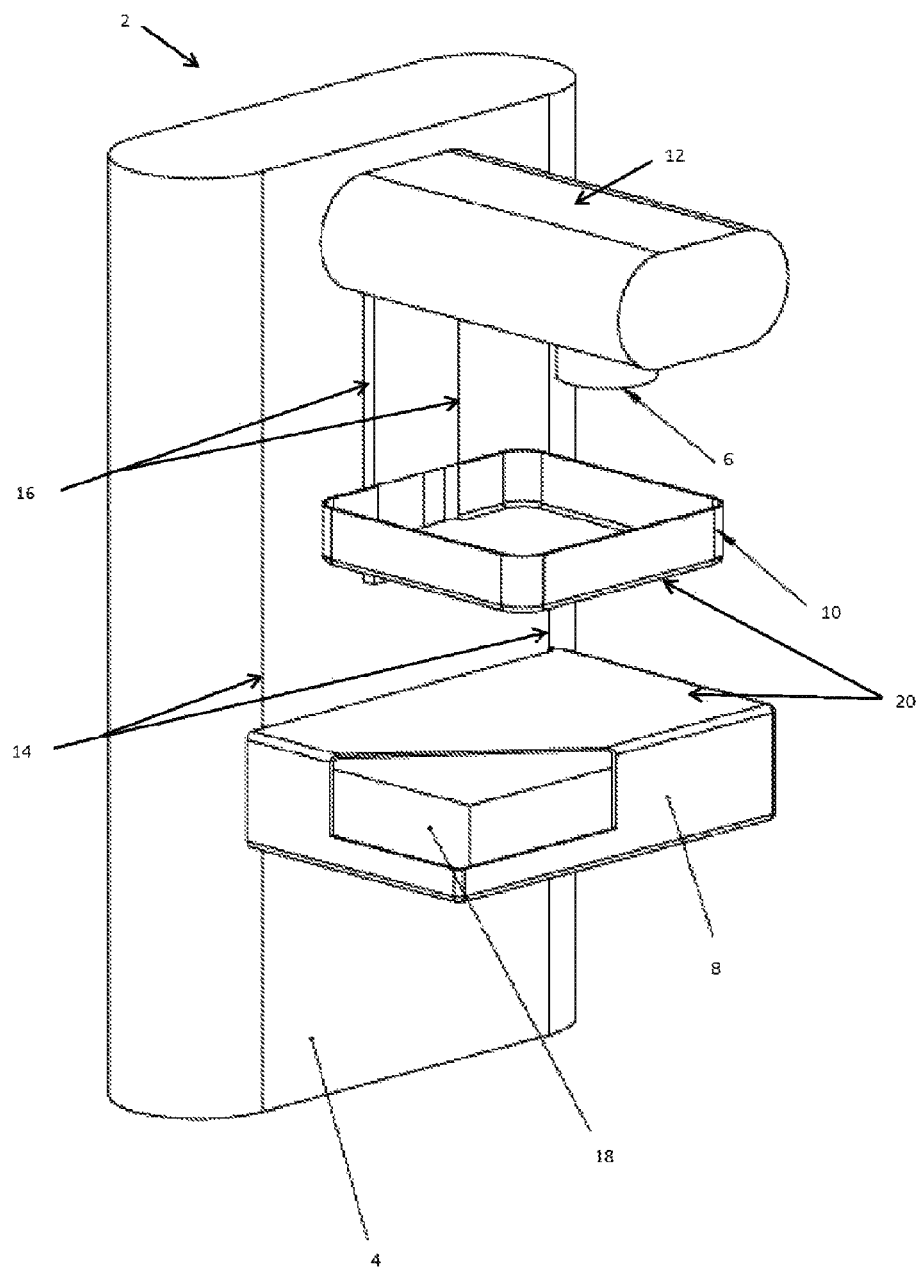
FIG. 1 is a perspective view of a mammography system comprising the heating laminates of the present application.

The present application relates to a heatable system suitable for use in a patient contacting plate used in medical imaging. The system comprises a heatable laminated structure with a plurality of layers each of which is transparent to imaging radiation and allows for thermal transfer. A heater layer, located between two of the plurality of layers, comprises an electrically resistive material and is transparent to imaging radiation. The laminated structure further includes a conductive path suitable for use in coupling a voltage source to the electrically resistive material in the heatable laminated structure, whereby the laminated structure is heated when current is passing through the conductive path.

A further aspect of the present application relates to a compression plate system for use in a medical imaging system. The compression plate system includes a pair of plates between which a patient or a portion of a patient to be imaged is placed and the heatable system of the present application is mounted on one or both of the pair of plates.

Another aspect of the present application relates to a medical imaging device including the compression plate system of the present application, a voltage source coupled to the conductive path, a source of radiation directed at the patient or the portion of the patient positioned between the compression plates, and an image generating unit to produce an image of the patient or the portion of the patient positioned between compression plates. The image results from radiation directed at the patient or the portion of the patient.

Embodiments of these aspects of the present application are shown in the drawings as described below.

FIG. 1 is a perspective view of a mammography system according to the present application. Mammography unit 2 includes stand 4, and X-ray unit 6. Height-adjustable breast platform 8 and compression plate 10, are both shown to have heating laminate 20 in FIG. 1; however, the heating laminate 20 can be incorporated in any one of breast platform 8 or compression plate 10. Suspension 12 supports X-ray unit 6. Breast platform 8 can be adjusted to the individual breast height of the patient by sliding it along tracks 14. In addition, compression plate 10 can be moved downwardly into compression contact with the patient's breast by sliding compression plate 10 along tracks 16. Breast platform 8, fits over digital x-ray detector 18 shown in the cutaway.

X-ray detector 18 is able to detect X-rays emitted during brief activation of X-ray emitter 6. As a result of such emission, an X-ray beam cone is produced and passes through compression plate 10, heating laminates 20, penetrates the breast lying on breast platform 8, and then into X-ray detector 18, creating a breast tissue-dependent absorption image. Breast platform 8 may include additional technical components well known to those skilled in the art.

Figure 2A:
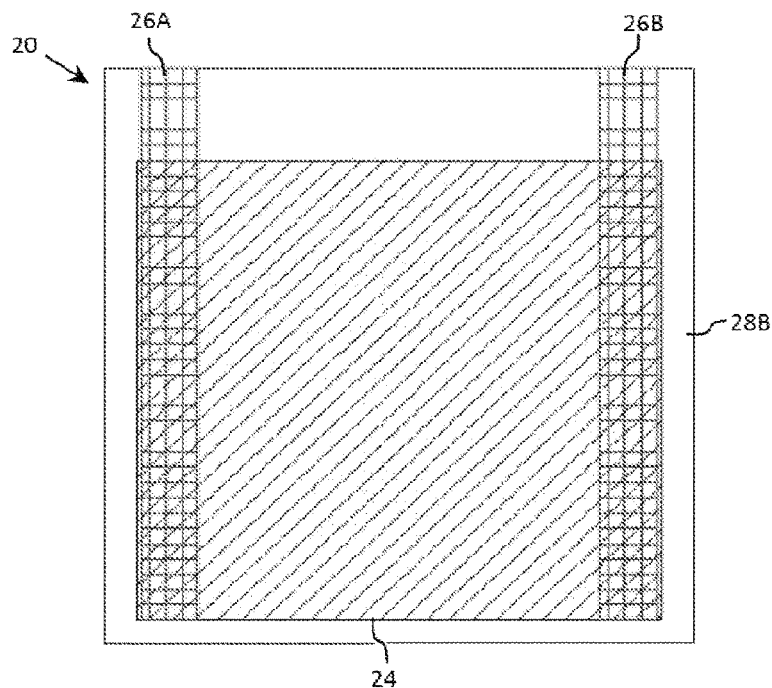
FIGS. 2A-2D show top and side views of a heating laminate according to the present application.
Figure 2B:
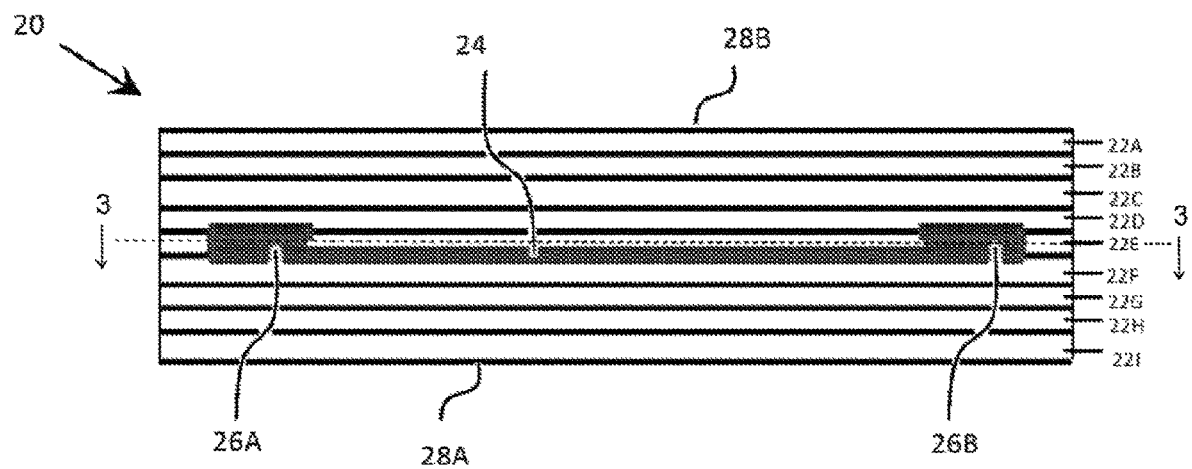

FIGS. 2A and 2B show the top, and side views, respectively, of heating laminate 20.

As illustrated, heating laminate 20 includes a plurality of layers 22A-22I, with surface 28A being proximate to layer 22I and surface 28B being proximate to layer 22A Each of layers 22A-22I can be formed of the same materials, substantially the same materials, or different materials, with each layer having the same or differing thicknesses. The layers may the plurality of layers are each fiber-containing composite layers. Additionally, as show in FIGS. 2C-2D, any of layers 22 can be replaced with insulative layers 23. Optionally, insulative layers 23 can be used in addition to layers 22.

Layers 22A-22I can be independently-formed layers of fiber-containing composites including cloth, mat, fiber, or paper. In a further embodiment the fiber-containing composites include carbon fibers.

The laminated structure of the present invention can be formed from layers of fiber composites, generally referred to as "prepregs". Prepregs are defined, for purposes of this application, as ready-to-mold material in sheet or layer form made of a fiber-containing polymer matrix. The matrix can be thermoset polymers, thermoplastic polymers, and combinations thereof. Examples of thermoset resins that may be used are: phenolics, polyesters, epoxies, bismaleimides, polyimides, and cyanates. Examples of thermoplastics are polystyrene, nylon, polycarbonate, acrylics, and vinyls.

Prepregs are stock items supplied to a fabricator who then "lay up" the material for production of a laminate, i.e., cuts the prepregs to a desired shape, layers them, and cures with heat and pressure. The resin in prepregs is normally partially cured to a "B-stage", i.e., a stage at which the resin is not completely cured but is tacky. However, prepregs may come in a variety of forms. For instance, prepregs may come as: 1) commercial prepregs, where the material is coated in a hot melt or solvent system according to customer requirements, and 2) wet prepreg, where the basic resin is installed without solvents or preservatives but has a limited room temperature shelf life (Vol. 1, Engineered Material Handbook, Composites, ASM International, page 19, which is hereby incorporated by reference in its entirety).

The fiber-containing composite layers each independently have a thickness ranging from 0.001 to 0.060 inches.

A prepreg layer, is cut to a desired shape and size, and is laid in a form or mold. If desired, a plurality of prepreg layers may simultaneously be made for efficiency. It is important to note that the shape and size of the layers may vary according to the particular setting in which the heating laminate is to be used. The heating laminate of the present application can therefore be formed in any shape or size necessary for their intended application.

After placement of a layer, such as intermediate layer 22F of the heating laminate structure, which is on top of layers 22G, 22H, and 22I, respectively, electrical resistive material layer 24 can be placed over some, or all of layer 22F. For example, electrical resistive material layer 24 is shown located adjacent to one side of heating laminate 20 and spaced from the other three lateral sides of heating laminate 20. Such a placement can be used, for example, when heating laminate structure 20 is aligned with one edge of electrical resistive material layer 24 the corresponding edge of the adjacent layer, but not with the other edges of that adjacent layer. However, it is understood that this is only illustrative. In other embodiments, electrical resistive material layer 24 can be spaced from, or aligned with, some or all of the edges of heating laminate 20. The particular size and location of electrical resistive material layer 24 can be selected based on the desired surface area to be heated, the thermal properties of electrical resistive material layer 24 and/or layers 22, and/or the like.

Electrical resistive material layer 24 can be formed of any suitable material, which will emit heat when an electrical current is applied to it and which allows imaging radiation to pass through it. For example, the radiation source can produce gamma rays, x-rays, radio waves, ultraviolet radiation, and/or the like, typically used during medical imaging applications. Suitable materials for electrical resistive material layer 24 are nickel-coated carbon, graphite, and graphene. Electrical resistive material layer 24 can have any suitable thickness, ranging from 0.0001 to 0.060 inches such as approximately 60 mils (1 mm) or less.

An increase in resistance of electrical resistive material layer 24 will permit use of a lower current in order to achieve the same power. In regard to thickness of electrical resistive material layer 24, by reducing the thickness to 8 gsm vs a thicker 34 gsm (grams per square meter) a decrease in the current requirements due to the increase in resistivity is achievable.

Additionally, electrical resistive material layer 24 can have a surface resistivity of 1 ohms/square or less. In other embodiments, electrical resistive material layer 24 has a surface resistivity between approximately 0.25 and 0.75 ohms/square with a DC current.

Electrical resistive material layer 24 can be located anywhere within the thickness of heating laminate 20. For example, as illustrated in FIG. 2B, electrical resistive material layer 24 can be centrally located within heating laminate structure 20. In this case, when layers 22A-22I are formed of the same materials, heat from electrical resistive material layer 24 will generally radiate to both surfaces 28A and 28B at approximately the same rate. Such a configuration can allow either surface 28A or 28B of heating laminate 20 to be effectively used as a heated contact surface.

In one embodiment, heating laminate structure 20 can be configured such that one of surfaces 28A or 28B will heat more readily than the other of those surfaces. In this case, the more readily heated surface can be used as the heated contact surface. For example, electrical resistive material layer 24 can be located closer to a surface, such as surface 28B, of heating laminate structure 20 that is configured to form a contact surface for a corresponding application. In one embodiment, layers 22A-22I can be configured such that one surface will heat more readily than the other surface. For example, layers formed of a material having a low thermal conductivity can be located on one side of electrical resistive material layer 24, while layers formed of a material having a high thermal conductivity can be located on the other side of electrical resistive material layer 24. In either case, the respective materials are transparent to imaging radiation.

Figure 2C:
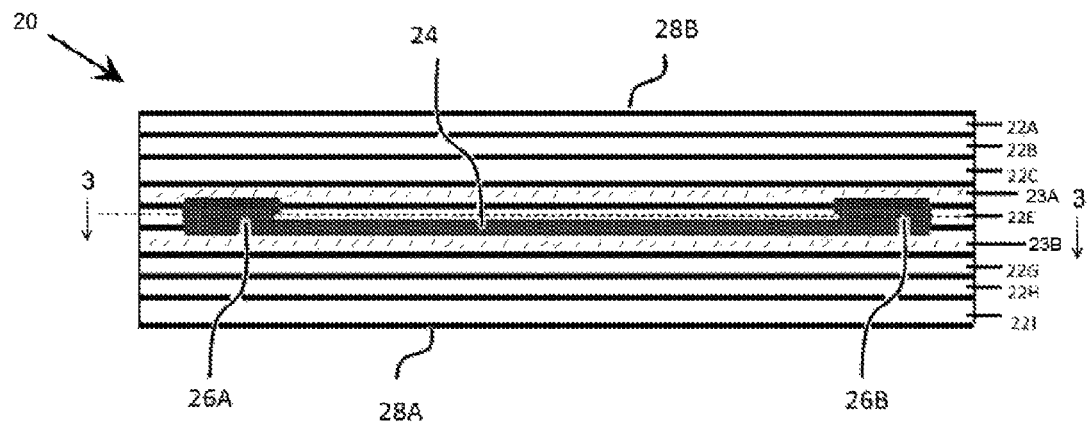
Figure 2D:
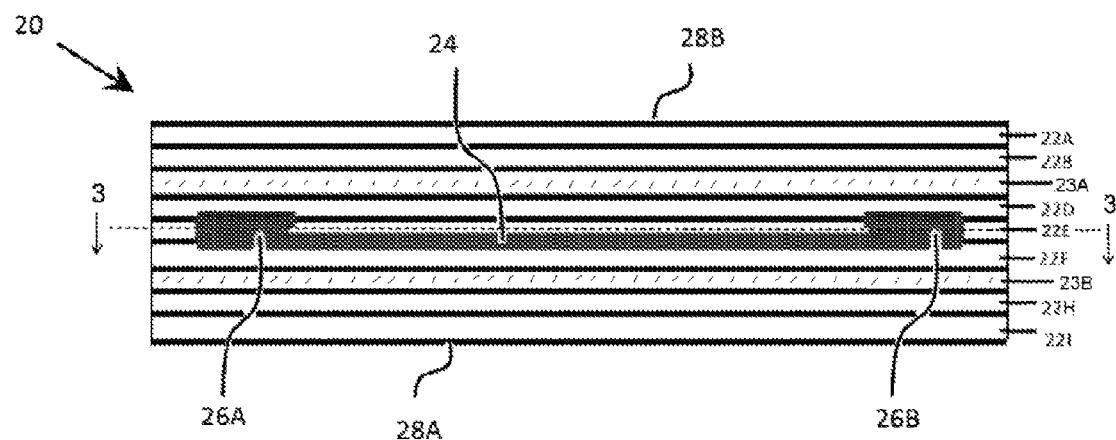

Optionally present in heating laminate 20 are one or more insulative layers 23, made from a material other than that of the plurality of layers (see FIGS. 2C-2D, and FIGS. 4C-4D). As shown in FIG. 2C the insulative layers 23A and 23B can be positioned directly above and below electrically resistive heating element 24. The insulative layers 23A-B can optionally be treated to laminate the electrically resistive material layer 24, and conductive elements 26A and 26B into a single fused unit. Additionally, as shown in FIG. 2D, insulative layers 23A and 23B may be positioned within heating laminate 20, replacing one or more of layers 22. Insulative layers 23 A-B can be made from polymers, including, but not limited to polyethylene terephthalate (PET), ethylene-vinyl acetate (EVA), and polyethylene (PE). Insulative layers 23A-B can range in thickness from 0.005 inches to 0.015 inches; however any thickness can be used so long as the heater is powerful enough to overcome the insulating effect of insulative layers 23A-B. In one embodiment, the plurality of layers include insulative layers surrounding the heater layer. The insulative layers can be made from material which include, but are not limited to polyethylene terephthalate, ethylene-vinyl acetate, or polyethylene.

A pair of conductive elements 26A and 26B can be located on opposing sides of electrical resistive material layer 24, as illustrated in FIGS. 2A-2D. Each of conductive element 26A and 26B can be substantially parallel to each other and extend across heating laminate 20. Furthermore, conductive elements 26A and 26B can be embedded in heating laminate 20, as shown in FIG. 2B, or exposed on one or both of the opposing side surfaces of heating laminate 20. It is also understood that conductive elements 26A and 26B can only partially extend across heating laminate 20. In another embodiment, conductive elements 26A and 26B can be spaced from all side surfaces of heating laminate 20. As illustrated, conductive elements 26A and 26B can extend beyond electrical resistive material layer 24. Alternatively, conductive elements 26A and 26B can be coextensive with a length of electrical resistive material layer 24 or be even shorter than the length of electrical resistive material layer 24.

Heating laminate 20 can be configured to enable an electrical connection to be made to conductive elements 26A and 26B. For example, conductive elements 26A and 26B can extend beyond a side surface of heating laminate 20 to allow coupling thereto, as seen in FIGS. 3A-D. In one embodiment, an electrical connection can be made to conductive elements 26A and 26B by, for example, drilling an opening into heating laminate 20 in a location aligned with conductive elements 26A and 26B. In any case, an electrical connector can be physically attached to each of conductive elements 26A and 26B. An exploded view of heating laminate 20 is shown in FIGS. 4A-4D. As illustrated in FIG. 4A, laminate layers 22A-I are stacked together with electrically resistive heating material layer 24 sandwiched between layers 22E and 22F. Conductive elements 26A and 26B are attached to electrically resistive heating material layer 24 before being placed into the laminate. FIG. 4B illustrates the electrically resistive heating element of FIG. 3E positioned between laminate layers 22E and 22F. FIG. 4C illustrates a heating laminate 20 with layers 22E and 22F replaced with insulative layers 23A and 23B. Similarly, FIG. 4D shows the heating laminate 20, with layers 22D and 22G replaced with insulative layers 23A and 23B.

Each of conductive elements 26A and 26B can be formed of a highly conductive material. In an illustrative embodiment, conductive elements 26A and 26B can be formed of a metal, such as a metallic mesh (e.g., a nonwoven metallic mesh), a conductive wire, or a solid metallic foil. Illustrative metals suitable for use include copper, aluminum, and/or the like. For example, an EMI shielding tape that has a tinned copper mesh with an aluminum polyester tape backing, (e.g., Zip-Mesh® (AL)), can be used as the conductive element. In one embodiment, each of conductive elements 26A and 26B has a thickness of 0.2 mm or less (e.g., as small as 0.02 mm). However, it is understood that a material having any thickness can be utilized. When conductive elements 26A and 26B comprises a mesh, the mesh can have an open area up to approximately 90%, such as between 60% and 80%. Conductive elements 26A and 26B can have a width of up to three centimeters.

Each of conductive elements 26A and 26B can directly contact electrical resistive material layer 24 to form an electrical contact therebetween. For example, electrical resistive material layer 24 can be bonded to conductive elements 26A and 26B. Alternatively, electrical resistive material layer 24 can be wrapped around each conductive elements 26A and 26B so that electrical resistive material layer 24 surrounds at least two sides of each of the conductive elements 26A and 26B and at least partially covers a third side of each conductive elements 26A and 26B. Alternatively, electrical resistive material layer 24 can completely surround four sides of each of each conductive elements 26A and 26B.

Figure 3A:
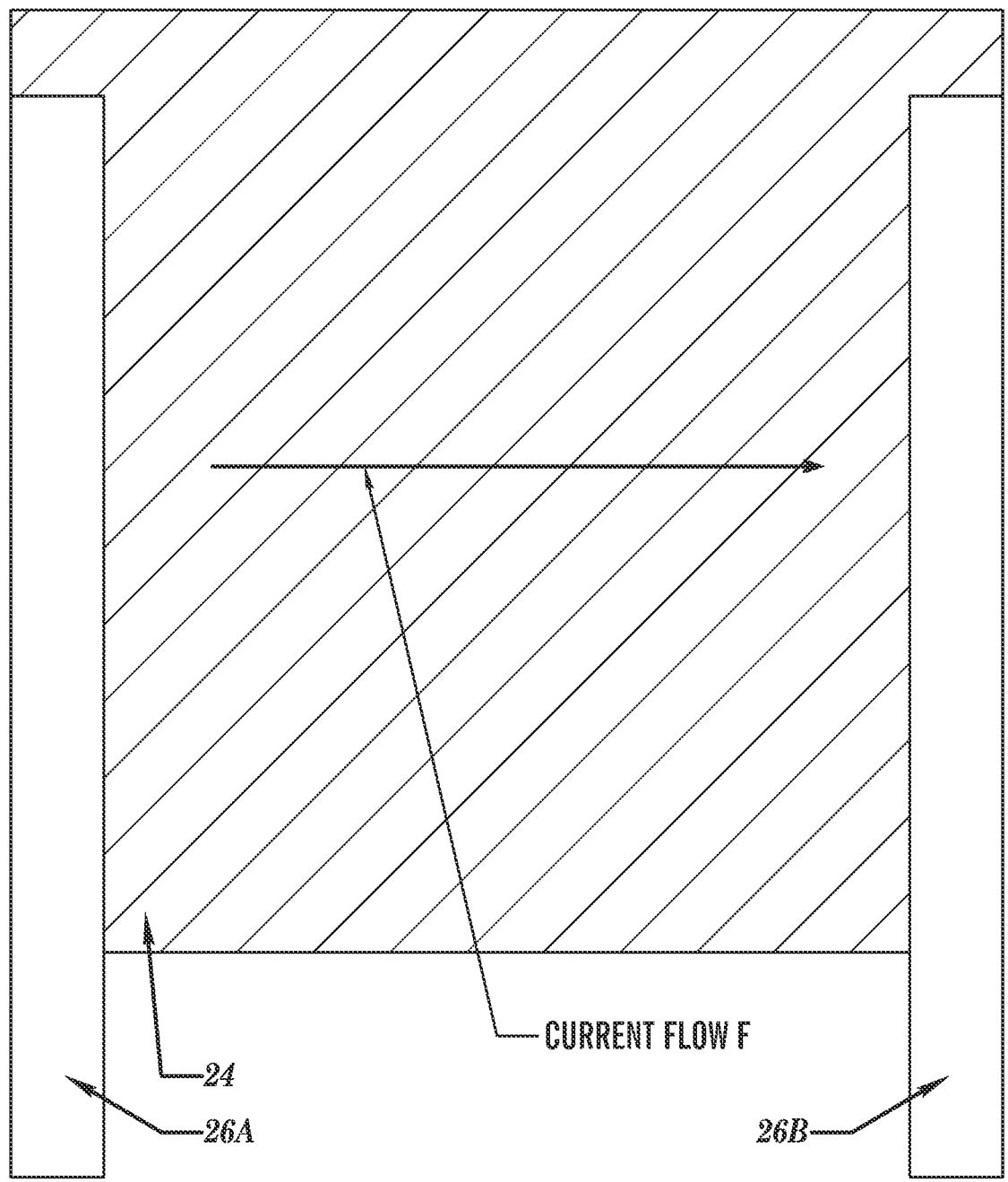
FIGS. 3A-E show top views of different embodiments of the electrically resistive heating material layer, each taken along line 3-3 of FIGS. 2B-2D.
Figure 3B:
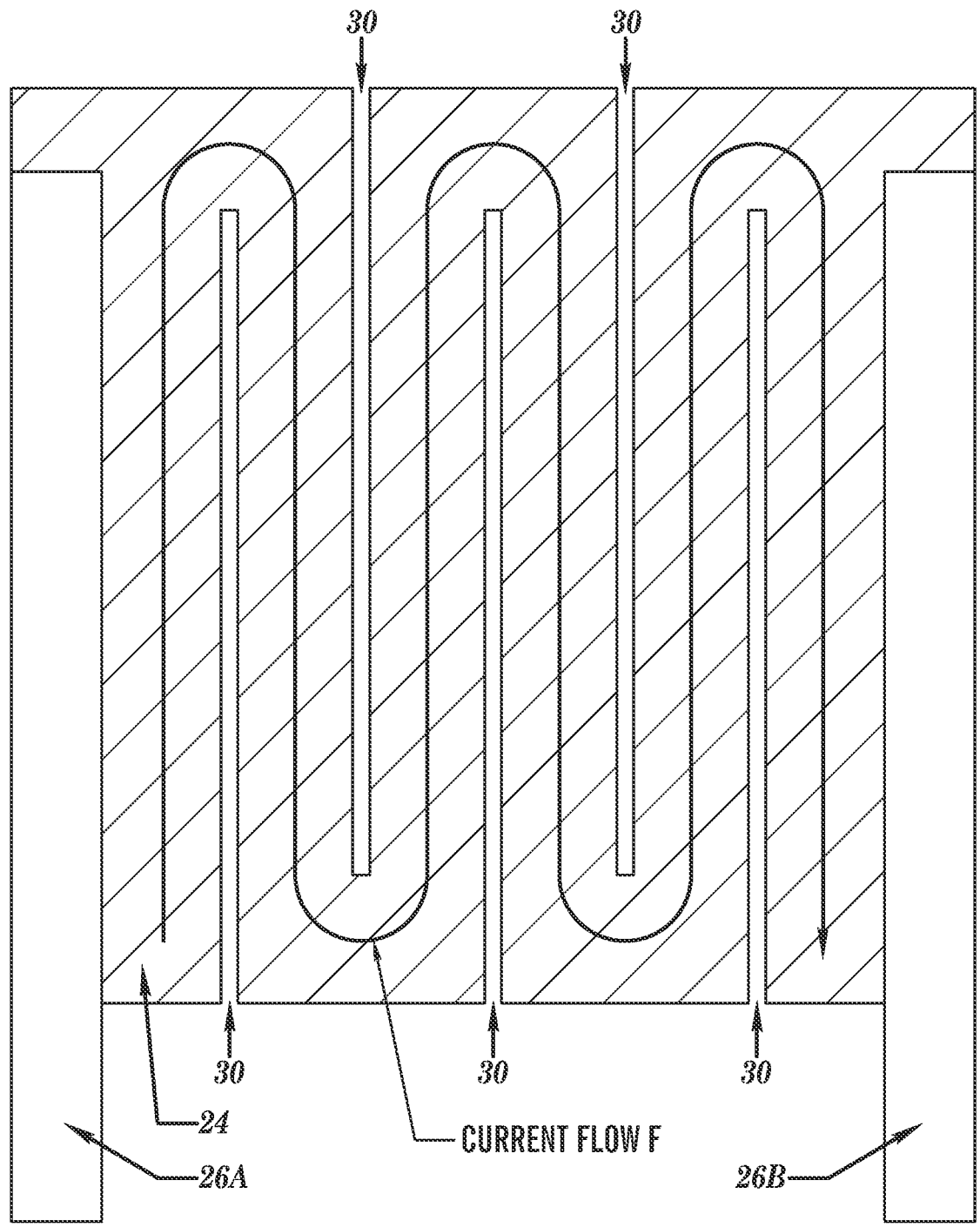
Figure 3C:
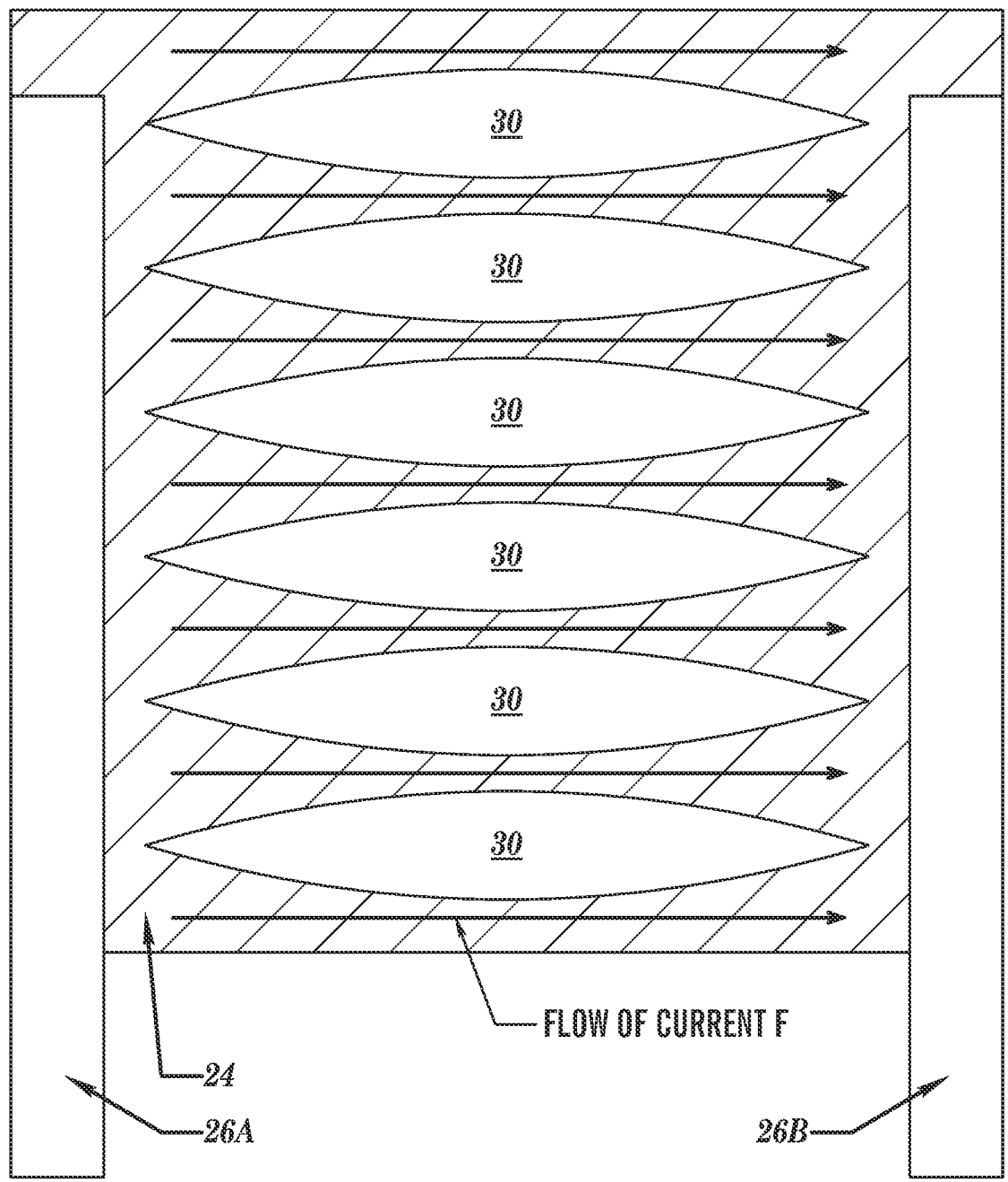
Figure 4A:
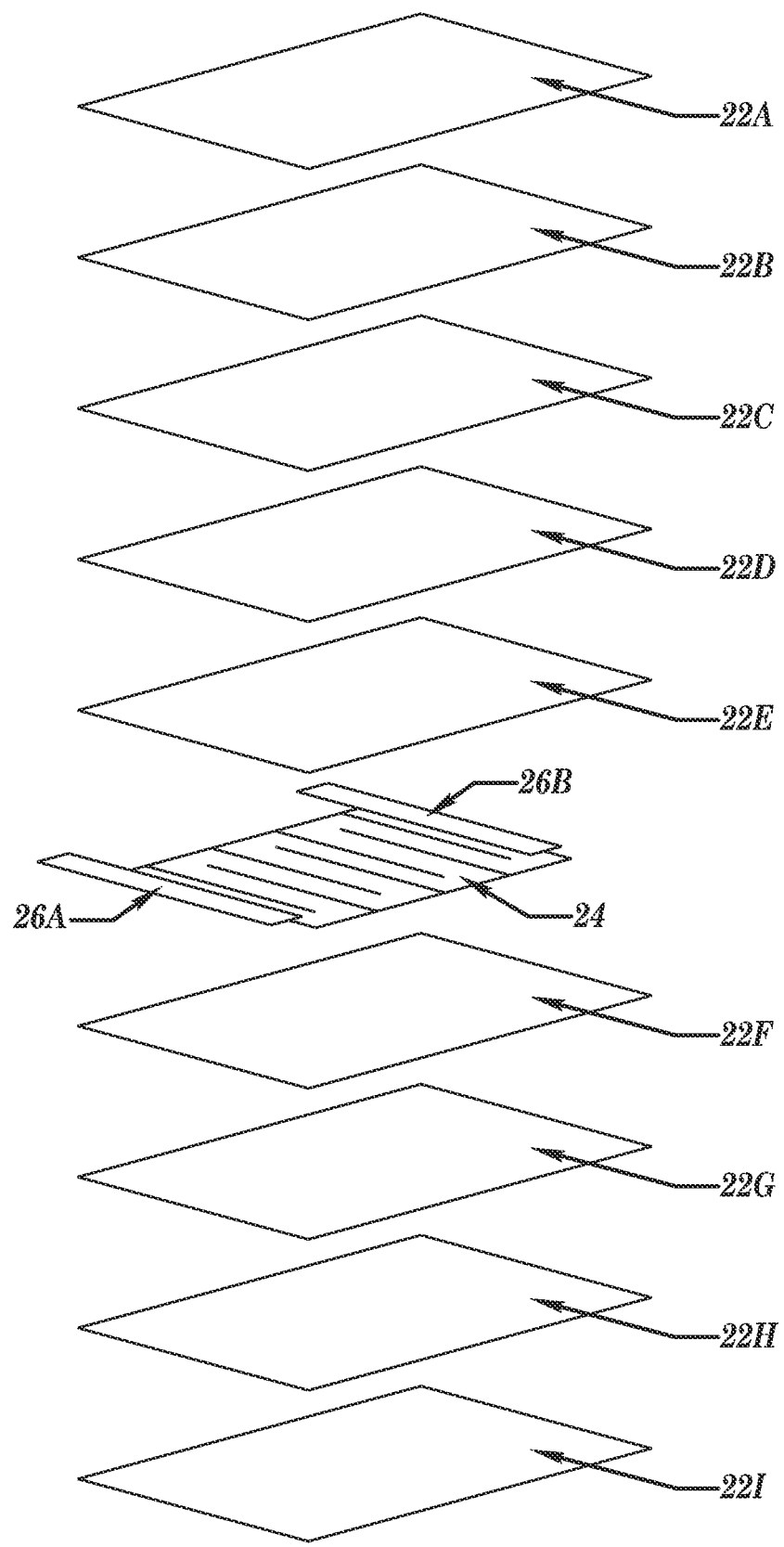
FIGS. 4A-D are exploded views of the heatable laminate of the present application including the electrically resistive heating material layer, and conductive path.
Figure 4B:
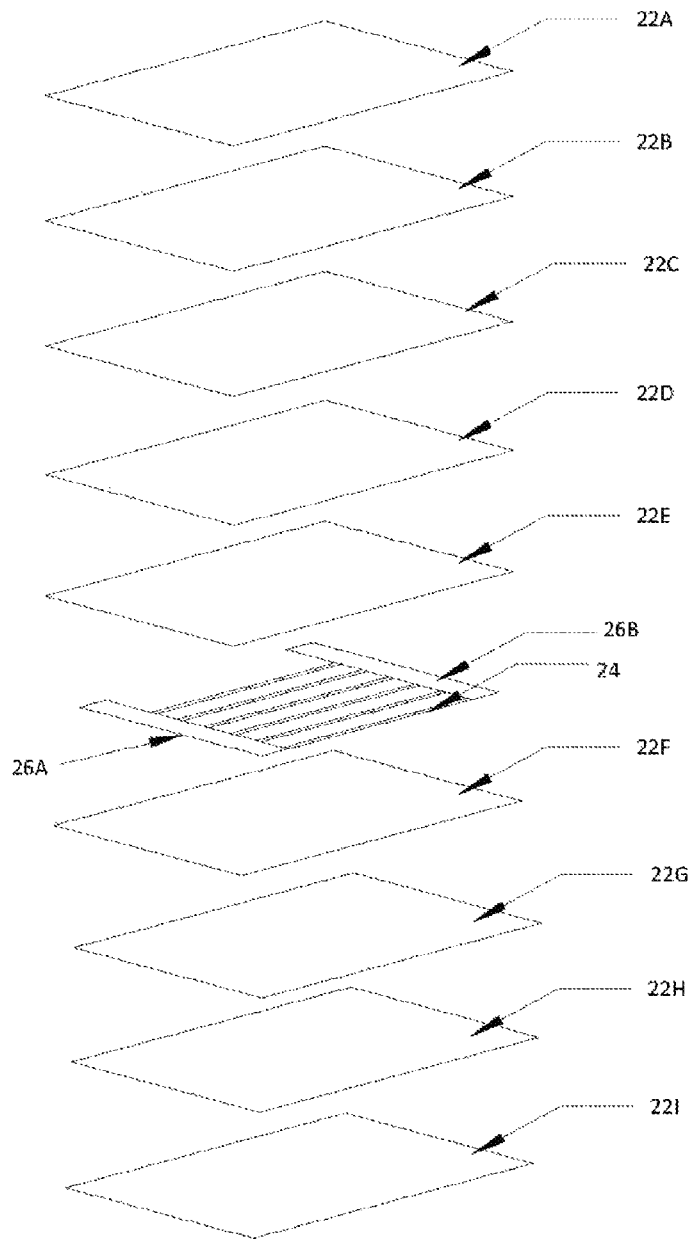
Figure 4C:
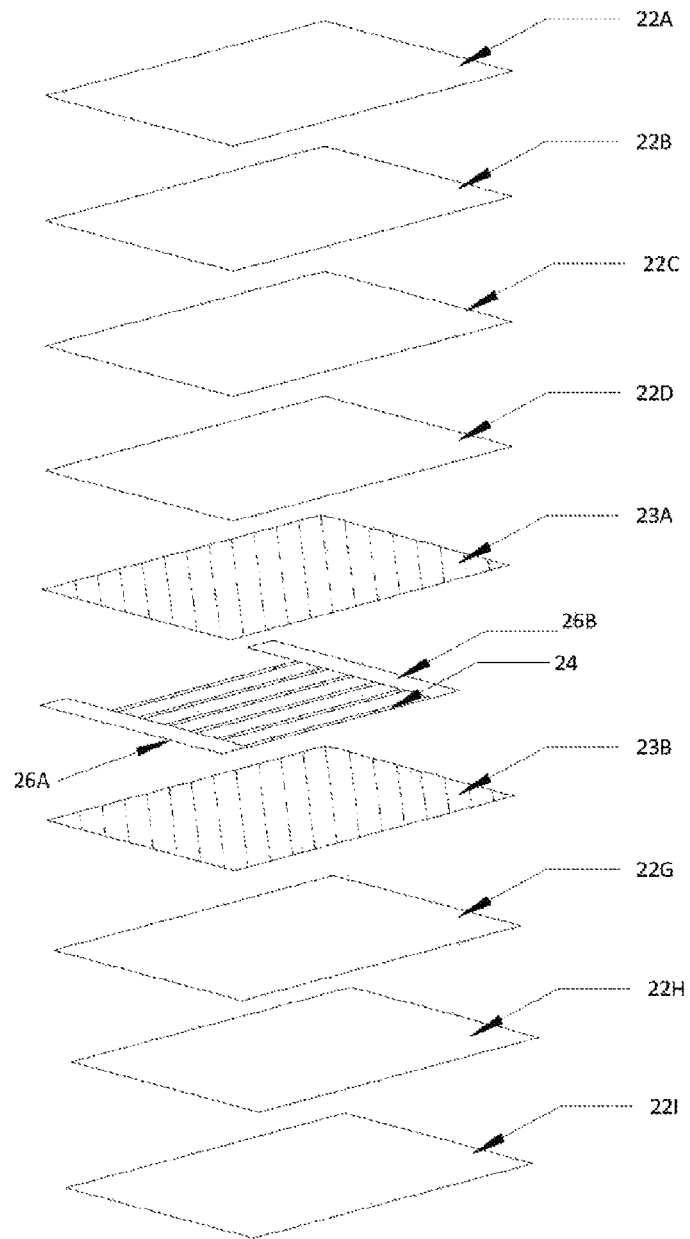
Figure 4D:
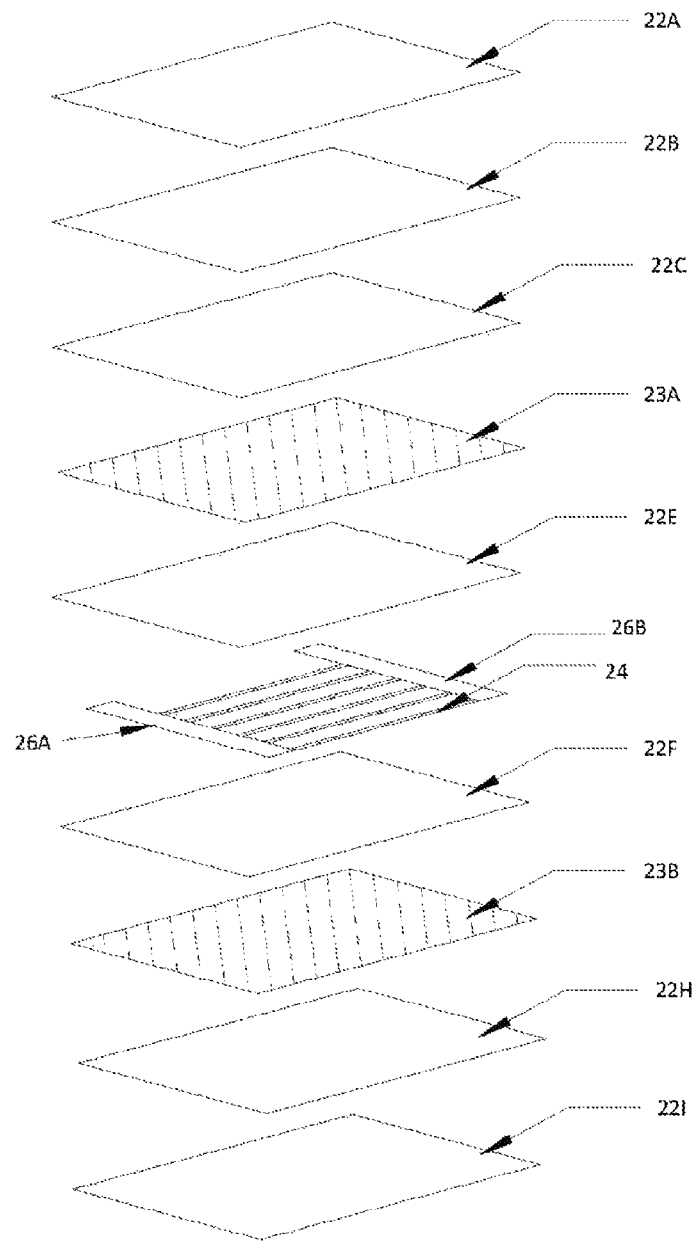

As shown in FIGS. 3A, 3B and 3C, conductive elements 26A and 26B are connected to opposite sides of electrical resistive material layer 24 and current flow F passes from conductive element 26A through electrical resistive material layer 24 to conductive element 26B to permit heating of that layer and of heating laminate 20 when current is applied to conductive elements 26A and 26B. Electrical resistive material layer 24 can be arranged in several ways to vary the distribution of heat in heating laminate 20 and the current supplied to conductive elements 26A and 26B.

FIG. 3A shows one embodiment where electrical resistive material layer 24 is a continuous sheet. This permits current flow F to move directly across electrical resistive material layer 24 between conductive elements 26A and 26B.

In other embodiments, electrically resistive material layer 24 has discontinuities or gaps to direct current flow F in a longer path between conductive elements 26A and 26B.

As shown in FIG. 3B, electrically resistive material layer 24 can have multiple discontinuations to create a circuitous path for current flow F. Electrical resistive material layer 24 in FIG. 3B has been cut to provide for gaps 40. This increases the length of the electrical path that current flow F must follow and allows for control of the heat distribution in heating laminate 20 and the electrical requirements for conductive elements 26A and 26B.

FIG. 3C shows electrical resistive material layer 24 with multiple paths of current flow F between conductive elements 26A to 26B. These paths, which are of varying cross section, controlled by the size and shape of gaps 30 in electrical resistive material layer 24, control the distribution of heat in heating laminate 20 and the electrical requirements supplied to conductive elements 26A and 26B.

Figure 3D:
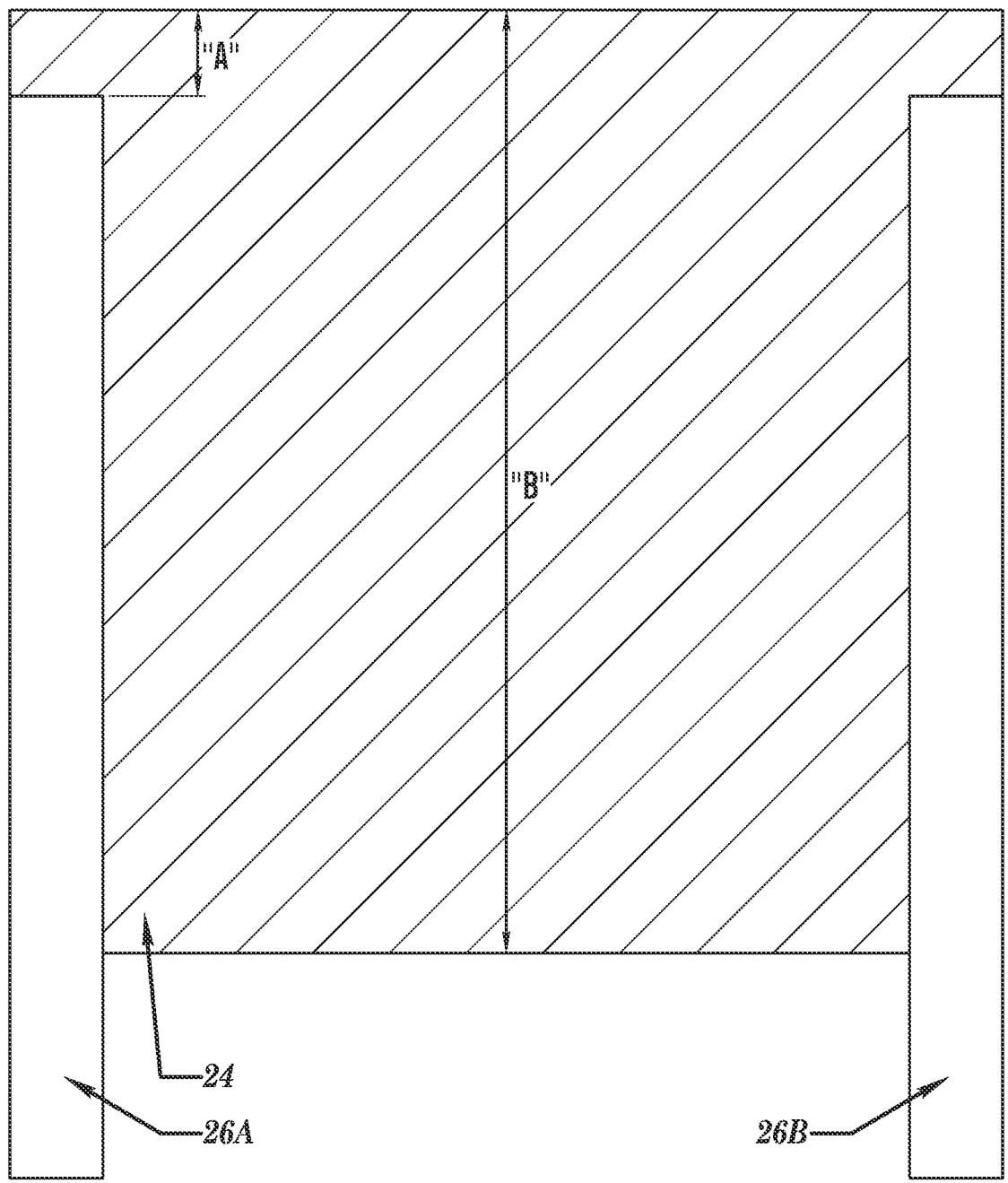

As shown in FIG. 3D, the connection overlap between electrical resistive material layer 24 and conductive path 26A and electrical resistive material layer 24 and conductive path 26B can be adjusted to reduce the dissipation of heat at the junction of electrical resistive material layer 24 and conductive path 26A and electrical resistive material layer 24 and conductive path 26B. As indicated in this figure, as A/B goes to zero, hot spots will be minimized at the junction of conductive elements 26A and 26B, and electrical resistive material layer 24. As A/B increases more heat will be generated at the junction of conductive elements 26A and 26B, and electrical resistive material layer 24. By increasing the area of the junction between electrical resistive material layer 24 and conductive elements 26A to 26B, heat is distributed over a larger area. This avoids a localized concentration of heat at the junction.

Figure 3E:
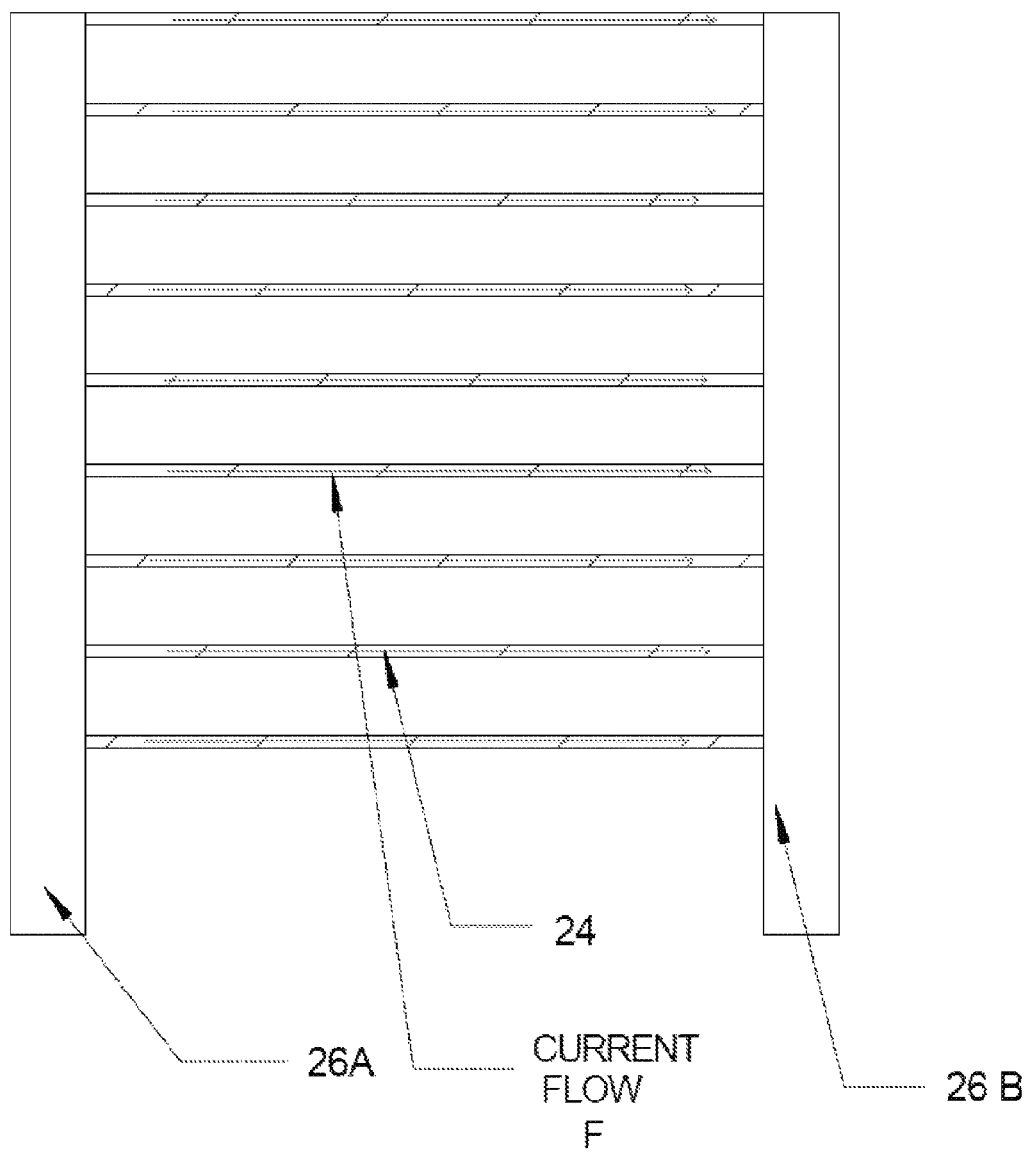

FIG. 3E shows a further embodiment, where the electrically resistive material layer 24 is made of thin strips of electrically resistive material with spaces positioned between them, creating multiple paths of current flow F between conductive elements 26A to 26B.

Yet another aspect of the present application relates to a method of forming a laminate through which radiation passes. The method includes providing a plurality of layers each of which is transparent to imaging radiation and allows for thermal transfer. A heater layer comprising an electrically resistive material which is also transparent to imaging radiation is also provided. The plurality of layers and the heater layers electrically resistive material layer are laminated together so that the heater layer is located between two of the plurality of layers to produce a heatable laminated structure. A conductive path is coupled to the electrically resistive material so that the laminated structure is heated when current is passing through the conductive path.

With reference to FIG. 4, heating laminate 20 can be prepared starting with layer 22A or layer 22I and sequentially adding the remaining layers 22B, 22C, 22D, 22E, 22F, 22G, and 22H, and/or insulative layers 23A and 23B, as well as electrically resistant material layer 24 to one side of either of those starting layers and laminating the applied layers together. Alternatively, heating laminate 20 can be fabricated by starting with one of the intermediate layers, adding layers on both sides of the starting layer, and laminating all of the applied layers together.

Although electrically resistant material layer 24 is shown embedded in a central portion of heating laminate 20, it is understood that electrically resistant material layer 24 and corresponding conductive elements 26A and 26B can be located anywhere along a thickness of heating laminate 20. Similarly, while heating laminate 20 is shown having a rectangular shape, it is understood that heating laminate 20 can have any desired shape and/or size.

Once the desired number of layers has been provided, the laminate can be completed by applying heat, in the range of 180-350° F. (depending on the materials chosen) and pressure to the layers, to complete any curing and to bond the layers together.

A further aspect of the present application relates to a method of imaging a patient or a portion of a patient. The method includes providing the medical imaging system of the present application and placing the patient or the portion of the patient to be imaged between the compression plate system. The patient or the portion of the patient to be imaged is heated by passing current through the electrically resistive material of the heatable laminate structure from the voltage source. The patient or the portion of the patient between the compression plates is imaged.

With reference to FIG. 1, the breast of a patient being given a mammography is placed on breast platform 8 which is raised or lowered along tracks 14 according to the standing or seating height of the patient. Next, compression plate 10 is lowered along tracks 16 into slight compression contact with the patient's breast on breast platform 8. As a result, the breast is distributed as evenly as possible on a surface of breast platform 8, which is as large as possible, to produce a higher resolution image and allow for better diagnosis. Compression plate 10 and breast platform 8 only serve to shape the breast and do not appear in the X-ray image, because they are transparent to imaging radiation.

Figure 6:
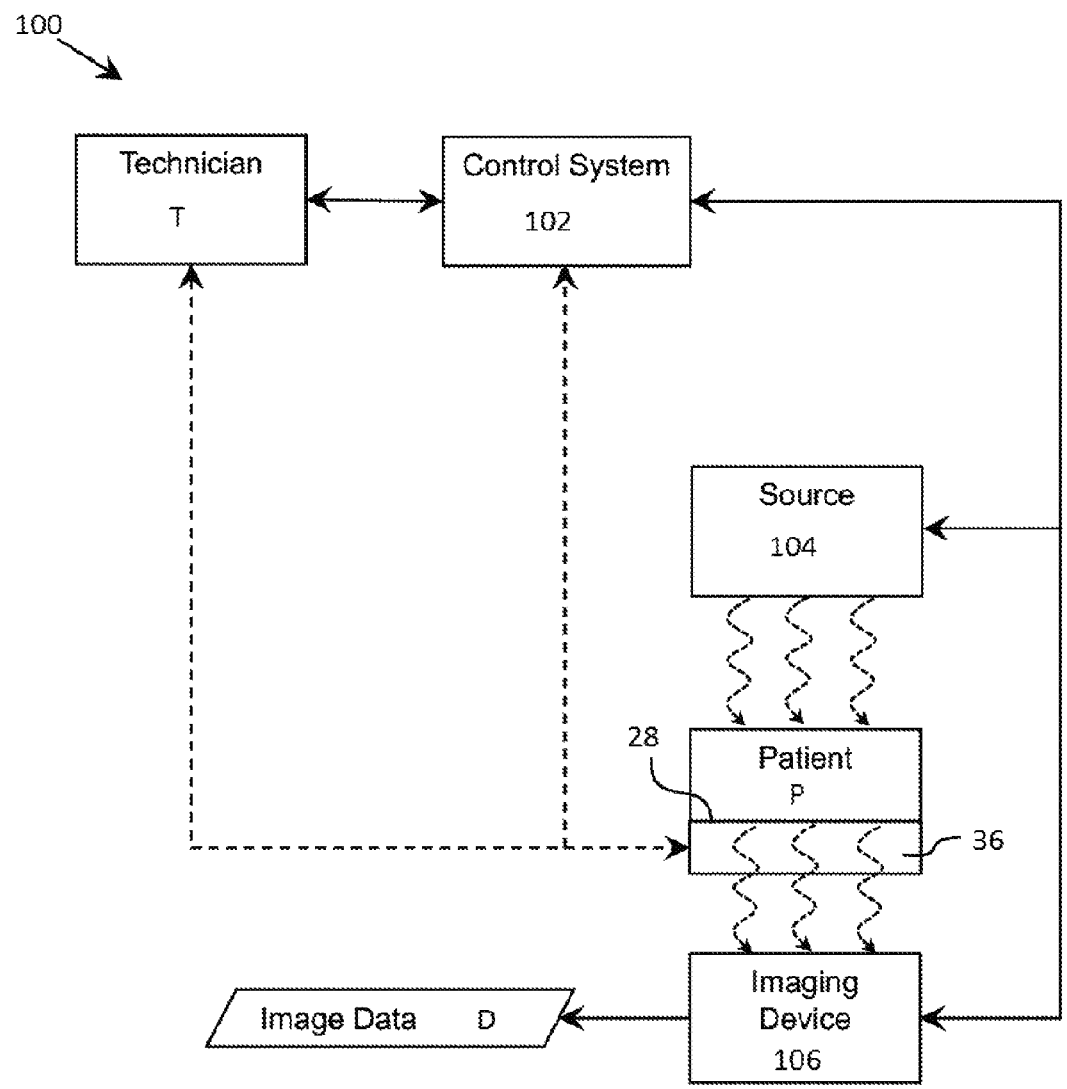
FIG. 6 shows a schematic view of a medical imaging system for acquiring image data of a patient utilizing the heated laminate of the present invention.

During use, at least one of surfaces 28A or 28B of heating laminate 20 can be heated to a desired temperature. To this extent, FIG. 6 is a schematic drawing of one embodiment showing heated contact surface system 36 according to the present application. Heated contact surface system 36 includes heating laminate 20, which is electrically connected to voltage source 40. When voltage source 40 supplies current to heating laminate 20, contact surface 28 is heated.

To this extent, voltage source 40 is electrically connected to each conductive elements 26A and 26B of heating laminate 20 to enable voltage source 40 to generate an electrical current that enters heating laminate 20 through one of conductive elements 26A and 26B and passes through the electrical resistive material layer 24. The electrical current generated by voltage source 40 can comprise either alternating current or direct current. Additionally, the current can flow in either direction through heating laminate 20 and can be continuous or pulsed. Voltage source 40 can be configured to generate a varying amount of current to enable a variable rate of heating to occur within heating laminate 20.

Voltage source 40 is operated by controller 44 which can acquire temperature data from temperature sensing unit 42, which can comprise one or more temperature sensors. The current sent by voltage source 40 to heating laminate 20 can be adjusted using the temperature data. For example, the current from voltage source 40 can be turned on or off, increased or decreased, and/or the like by controller 44, based on a difference between the sensed temperature and a target temperature for heated contact surface 28.

Temperature sensing unit 42 can comprise any number of one or more types of temperature sensors, which can acquire data corresponding to a temperature of heated contact surface 28 of heating laminate 20 for processing controller 44, which controls power source 40. Illustrative temperature sensors include a thermistor, a resistance thermometer, a thermocouple, a semiconductor-based temperature sensor, an infrared temperature sensor, etc. One or more temperature sensors may be integrated into heating laminate 20. For example, a temperature sensor can be located between two layers of heating laminate 20, e.g., between a layer forming the heated contact surface 28 and a layer adjacent to the top layer. Alternatively, the temperature sensor can be located adjacent to heating laminate 20. In one embodiment of all aspects of the present application, the heating system includes a temperature sensor and a regulator which controls the flow of current through the conductive path in response to signaling from the temperature sensor.

Regardless, temperature sensing unit 42 can be configured to provide temperature data regarding one or more target regions of heated contact surface 28. The temperature data should have accuracy suitable for a given application. For example, the temperature data corresponding to a central region of heated contact surface 28 of heating laminate 20 can have an accuracy within ±5 degrees Celsius. However, it is understood that the temperature(s) can be taken at any location(s) of heated contact surface 28 of heating laminate 20.

Voltage source 40 can be any type of power source. For example, voltage source 40 can comprise a set of batteries. Alternatively, voltage source 40 can comprise an electrical power interface for acquiring power from an external source of power, such as an electrical connector, a wall plug, and/or the like. Regardless, voltage source 40 can comprise any combination of electrical components configured to switch between two or more power sources, convert power to a type of power used by the heating unit 52, and/or the like.

Controller 44 can comprise any type of interface that provides information to user U and/or enables user U to operate voltage source 40. For example, controller 44 can inform user U of an operating status, a temperature of the heated contact surface 28 of heated laminate 20, and/or the like. Additionally, controller 44 can enable user U to selectively turn on/off voltage source 40, adjust a target temperature for heated contact surface 28 of heating laminate 20, and/or the like. User U can comprise a human user or a system user. In the latter case, controller 44 can be configured to communicate with user U using any type of communications interface.

FIG. 6 shows illustrative medical imaging system 100 for acquiring image data D of a patient P. The entire body of patient P can be imaged or any portion thereof. Regardless, a portion of patient P can contact heated contact surface 28 of the laminated structure of heated contact surface system 26. The skin of patient P can directly contact heated contact surface 28 or a layer of material (e.g., a hospital gown) may be present between the skin of patient P and heated contact surface 28.

As illustrated, medical imaging system 100 can include imaging device 106 (e.g., a camera, a digital detector, photographic film, and/or the like) for acquiring image data D of patient P. Imaging device 106 can generate the image data based on interaction of radiation generated by source 104 with patient P. As illustrated, radiation may be altered as it passes through patient P before being imaged by imaging device 106. Alternatively, the radiation can reflect off of patient P and be sensed by the imaging device 106. In either case, heating laminate 20 (FIGS. 2A-2D), including the heated contact surface 28, can be transparent to the radiation, thereby not altering the image generated by imaging device 106. If conductive elements 26A and 26B may alter the image generated by imaging device 106, the locations of conductive elements 26A and 26B can be selected so that the image data corresponding to these locations is not relevant to evaluating patient P when heating laminate 20 is properly positioned with respect to patient P.

Imaging device 106 and source 104 can be controlled by a control system 108 to generate radiation and acquire image data D. Control system 108 can be operated by technician T who can assist patient P in getting properly positioned prior to acquiring image data D. As part of a procedure for acquiring image data D, heated contact surface system 36 first can be operated to heat heated contact surface 28 for patient P to a predetermined temperature. Subsequently, patient P can be positioned with respect to contact surface 28 for imaging. It is understood that while medical imaging system 100 is shown including only a single heated contact surface system 36, any number of heated contact surface systems 36 can be utilized. For example, when a body part of patient P to be imaged requires compressing (e.g. in mammography), heated contact surface system 36 can be used on both sides of the body part. Heating contact surface 28 can be turned off before patient P is positioned and/or before the image data is acquired or remains on through imaging patient P.

Figure 5:
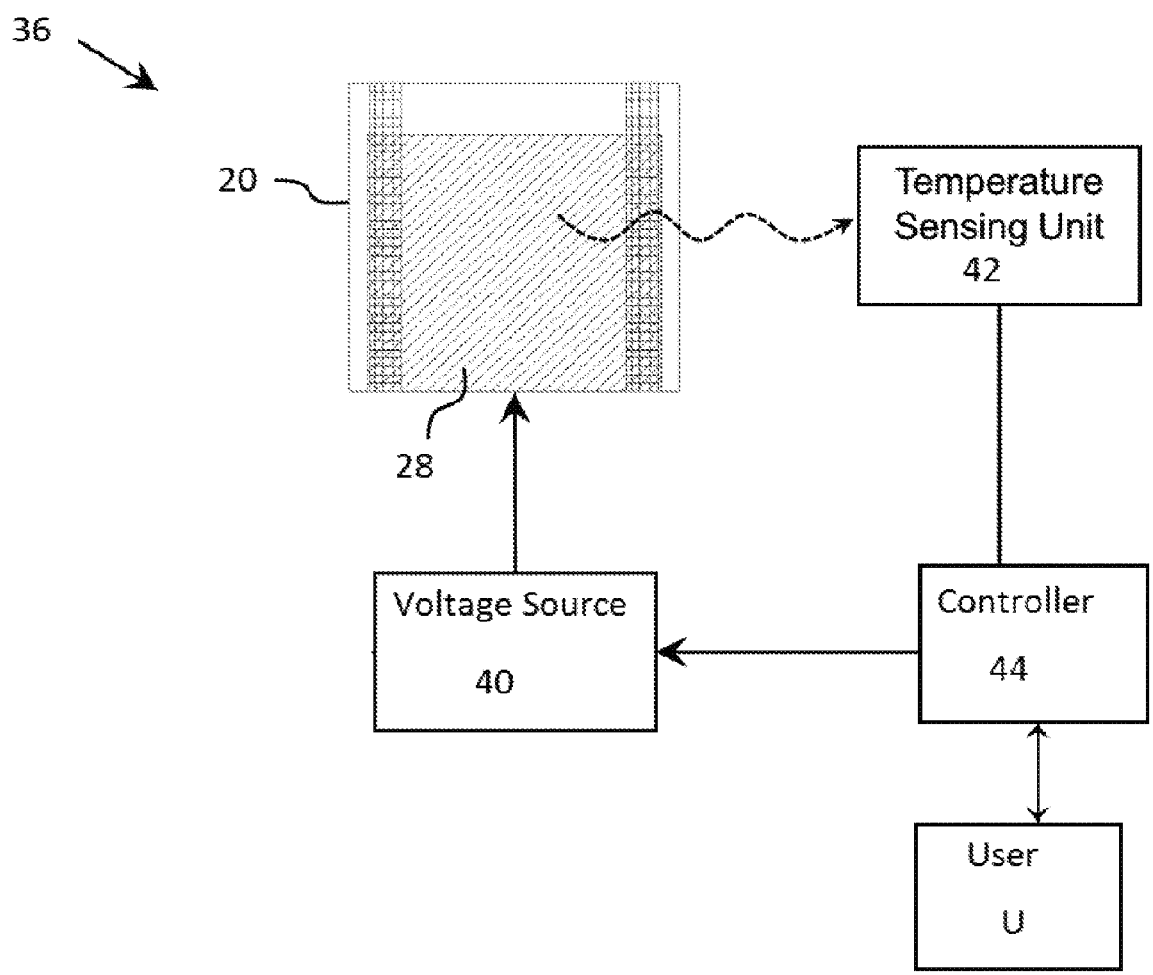
FIG. 5 shows a schematic of the heated contact surface system of the present application.

As illustrated, heated contact surface system 36 can be operated by control system 102 and/or technician T. In the former case, heated contact surface system 36 can be integrated with medical imaging system 100. To this extent, control system 102 can implement some or all of the actions described in conjunction with voltage source 40 (FIG. 5) of heated contact surface system 36. In the latter case, heated contact surface system 36 can be implemented apart from the remainder of medical imaging system 100 and operated independently thereof. However, it is understood that medical imaging system 100 could provide power for operating voltage source 40 via an electrical power interface.

Image data D can comprise any type of image data, such as digital image data, which is stored and accessed on a computer system, film image data, and/or the like. Additionally, imaging device 106 can generate image data from any type of radiation. To this extent, source 104 can generate any type of radiation suitable for use with imaging device 106. In one embodiment, the radiation is x-ray radiation. To this extent, medical imaging system 100 can comprise any type of radiological machine, such as a mammogram machine, an x-ray machine, and/or the like. As discussed above, in an illustrative embodiment, medical imaging system 100 is a mammogram machine and a breast of patient P is imaged while in contact with the heated contact surface 28.

Each of control system 102 and controller 44 (FIG. 5) can comprise one or more of any of various types of computing devices. In one embodiment, control system 102 and/or controller 44 comprises one or more general purpose computing devices executing program code to perform a process described herein. However, it is understood that embodiments of control system 102 and/or controller 44 can comprise special purpose hardware, with or without program code, configured to perform a process described herein. While control system 102 and controller 44 can be implemented separately, it is understood that the function of both can be implemented on the same computer system.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed is:

1. A heatable system suitable for use in a patient contacting plate for medical imaging, the heatable system comprising:
    a heatable laminated structure comprising:
        a plurality of insulative layers, each of which is transparent to imaging radiation and allows for a thermal transfer, wherein the plurality of insulative layers comprises polyethylene terephthalate, ethylene-vinyl acetate, or polyethylene;
        a heater layer located between two of the plurality of insulative layers, wherein the heater layer comprises an electrically resistive material selected from the group consisting of nickel-coated carbon, graphite, and graphene and is transparent to imaging radiation; and
        a conductive path formed from a nonwoven metallic mesh, a metal foil, or a conductive wire, suitable for use in coupling a voltage source to the electrically resistive material in the heater layer, whereby the heatable laminated structure is heated when a current is passing through the conductive path.

2. The heatable system of claim 1, wherein the plurality of insulative layers are fiber-containing composite layers.

3. The heatable system of claim 2, wherein the fiber-containing composite layers comprise a fiber-containing polymer matrix, wherein the fiber-containing polymer matrix is selected from the group consisting of thermoset polymers, thermoplastic polymers, and combinations thereof.

4. The heatable system of claim 3, wherein the fiber-containing polymer matrix is a thermoset polymer.

5. The heatable system of claim 3, wherein the fiber-containing polymer matrix is a thermoplastic polymer.

6. The heatable system of claim 2, wherein the fiber-containing composite layers are independently formed layers of fiber-containing composites comprising cloth, mat, fiber, or paper.

7. The heatable system of claim 6, wherein the fiber-containing composite layers comprise carbon fibers.

8. The heatable system of claim 2, wherein each of the fiber-containing composite layers independently has a thickness ranging from 0.001 to 0.060 inches.

9. The heatable system of claim 1, wherein the heater layer has a thickness ranging from 0.0001 to 0.060 inches.

10. The heatable system of claim 1, further comprising:
    a voltage source coupled to the conductive path.

11. The heatable system of claim 10, further comprising:
    a temperature sensor; and
    a controller which controls a flow of the current through the conductive path in response to signaling from the temperature sensor.

12. The heatable system of claim 1, wherein the electrically resistive material is a continuous sheet.

13. The heatable system of claim 1, wherein the electrically resistive material is a sheet with discontinuities.

14. The heatable system of claim 1, wherein the electrically resistive material is a sheet with multiple discontinuities to create longer current flow paths.

15. A compression plate system for use in a medical imaging system, the compression plate system comprising:
    a pair of plates between which a patient or a portion of a patient to be imaged is placed; and
    a heatable system of claim 1 mounted on one or both of the pair of plates.

16. The compression plate system of claim 15, further comprising:
    a voltage source coupled to the conductive path.

17. The compression plate system of claim 16, further comprising:
    a temperature sensor; and
    a controller which controls a flow of the current through the conductive path in response to signaling from the temperature sensor.

18. A medical imaging device comprising:
    a compression plate system of claim 15;
    a voltage source coupled to the conductive path;
    a source of radiation directed at the patient or the portion of the patient positioned between the pair of plates; and
    an image generating unit to produce an image of the patient or the portion of the patient positioned between the pair of plates resulting from radiation directed at the patient or the portion of the patient.

19. The medical imaging system of claim 18, wherein the source of radiation produces x-rays, gamma rays, radio waves, or ultraviolet radiation.

20. The medical imagining system of claim 19, wherein the source of radiation produces x-rays.

21. The medical imaging system of claim 18, wherein the medical imaging device is configured to carry out mammography.

22. The medical imaging system of claim 18, further comprising:
    a temperature sensor; and
    a control system which controls a flow of the current through the conductive path in response to signaling from the temperature sensor.

23. A method of imaging a patient or a portion of a patient, the method comprising:
    providing a medical imaging system of claim 18;
    placing the patient or the portion of the patient to be imaged between the pair of plates;
    heating the patient or the portion of the patient to be imaged by passing a current through the electrically resistive material of the heatable laminated structure from the voltage source; and imaging the patient or the portion of the patient between the pair of plates.

24. A method of forming a laminate through which radiation passes, the method comprising:
providing a plurality of insulative layers, each of which is transparent to imaging radiation and allows for a thermal transfer, wherein the plurality of insulative layers comprises polyethylene terephthalate, ethylene-vinyl acetate, or polyethylene;
providing a heater layer comprising an electrically resistive material selected from the group consisting of nickel-coated carbon, graphite, and graphene, which is transparent to imaging radiation;
laminating the plurality of insulative layers and the heater layer together so that the heater layer is located between two of the plurality of insulative layers to produce a heatable laminated structure; and
coupling a conductive path selected from the group consisting of nickel-coated carbon, graphite, and graphene, to the electrically resistive material so that the heatable laminated structure is heated when a current is passing through the conductive path.

\* \* \* \* \*